US00PP27395P2

(12) United States Plant Patent
Probst

(10) Patent No.: US PP27,395 P2
(45) Date of Patent: Nov. 15, 2016

(54) ***COREOPSIS* PLANT NAMED 'PEACH SPARKLE'**

(50) Latin Name: ***Coreopsis* hybrid**
Varietal Denomination: Peach Sparkle

(71) Applicant: Darrell R. Probst, Hubbardston, MA (US)

(72) Inventor: Darrell R. Probst, Hubbardston, MA (US)

( * ) Notice: Subject to any disclaimer, the term of this patent is extended or adjusted under 35 U.S.C. 154(b) by 8 days.

(21) Appl. No.: 14/545,429

(22) Filed: May 4, 2015

(51) Int. Cl.
*A01H 5/02* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Penny J. Aguirre

(57) ABSTRACT

A new cultivar of hybrid *Coreopsis* plant named, 'Peach Sparkle', that is characterized by its densely branched, compact, sturdy plant habit, its small, nearly sterile inflorescences with ray florets that are soft yellow in color with a large maroon eye, its floriferous and long bloom season that does not require deadheading, its cold hardiness at least to U.S.D.A. Zone 5, and its resistance to powdery mildew and leaf spot.

2 Drawing Sheets

Botanical classification: *Coreopsis* hybrid.
Variety denomination: 'Peach Sparkle'.

BACKGROUND OF THE INVENTION

The present invention relates to a new and distinct cultivar of *Coreopsis* plant of hybrid origin and botanically known as *Coreopsis* 'Peach Sparkle'. The new cultivar will be referred to hereafter by its cultivar name 'Peach Sparkle'. 'Peach Sparkle' is an herbaceous perennial grown for landscape and container use.

The new invention arose from an ongoing controlled breeding program in Hubbardston, Mass. The objective of the breeding program is to develop hybrid cultivars of *Coreopsis* with unique and superior garden attributes. In particular, to develop long-lived cultivars, in a wide range of flower colors and plant forms, that are sturdy, exhibit a true perennial habit, and are cold hardy to at least U.S.D.A. Zone 5.

The new cultivar arose from a cross made by the Inventor in August of 2011 in his test garden in Hubbardston, Mass. between an unnamed, proprietary plant in the Inventor's breeding program, reference no. J 06-1 (not patented), as the female parent and pollen that was pooled from a variety of unnamed, proprietary plants (not patented) from his breeding program as the male parent (all nearly sterile). The exact male parentage is therefore unknown. 'Peach Sparkle' was selected in September of 2012 as a single unique plant amongst the resulting seedlings.

Asexual propagation of the new cultivar was first accomplished by stem cuttings under the direction of the Inventor in Kensington, Conn. in September of 2012. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Peach Sparkle' as unique cultivar of *Coreopsis*.

1. 'Peach Sparkle' exhibits a densely branched, compact, sturdy plant habit reaching an average of 45 cm in height and width.
2. 'Peach Sparkle' exhibits small, nearly sterile inflorescences with ray florets that are soft yellow in color with a large maroon eye.
3. 'Peach Sparkle' exhibits a floriferous and long bloom season that does not require deadheading, beginning in early July and lasting until frost in Kensington, Conn.
4. 'Peach Sparkle' exhibits cold hardiness at least to U.S.D.A. Zone 5.
5. 'Peach Sparkle' exhibits resistance to powdery mildew and leaf spot.

The female parent of 'Peach Sparkle', J 06-1, differs from 'Peach Sparkle' in having flowers that are bright yellow in color, in being taller in height, and in having stems that tend to flop. 'Peach Sparkle' can be compared to the *Coreopsis* cultivars 'Bengal Tiger' (U.S. Plant Pat. No. 25,345) and 'Route 66' (U.S. Plant Pat. No. 20,609). 'Bengal Tiger' is similar to 'Peach Sparkle' in having a compact plant habit and inflorescences with ray florets that are yellow with a red eye. 'Bengal Tiger' differs from 'Peach Sparkle' in having inflorescences with ray florets that are deeper yellow in color with a red eye and in being susceptible to powdery mildew when grown under similar conditions in Massachusetts. Route 66' is similar to 'Peach Sparkle' in having inflorescences with ray florets that are yellow in color with a red eye. 'Route 66' differs from 'Peach Sparkle' in having inflorescences with ray florets that are darker yellow in color with an eye zone that is redder in color, in being very fertile and producing an abundance of seeds, and in being susceptible to powdery mildew when grown under similar growth conditions in Massachusetts.

BRIEF DESCRIPTION OF THE DRAWINGS

The accompanying colored photographs illustrate the overall appearance and distinct characteristics of the new

*Coreopsis*. The photographs were taken of a three month-old plant of 'Peach Sparkle' as grown outdoors in a one-gallon container from a 30-cell plug in Kensington, Conn.

Figure 1:
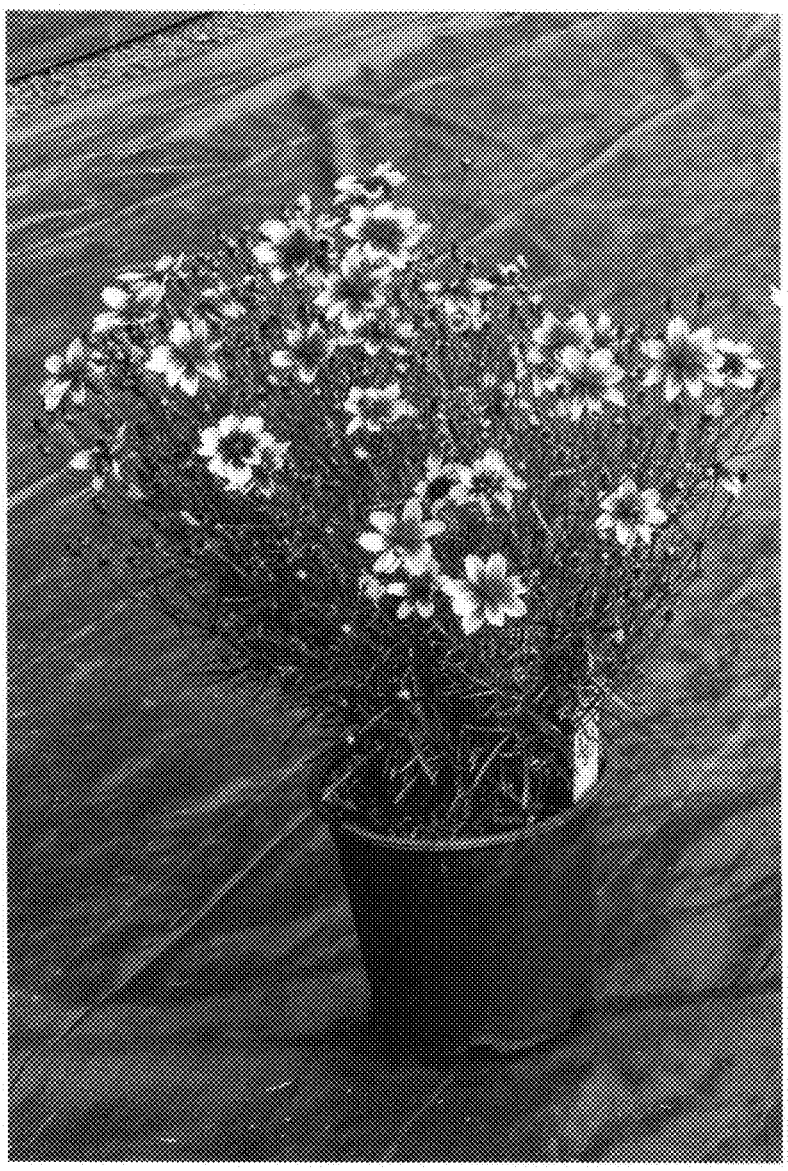

The photograph in FIG. 1 provides a side view of a plant of 'Peach Sparkle' in bloom.

Figure 2:
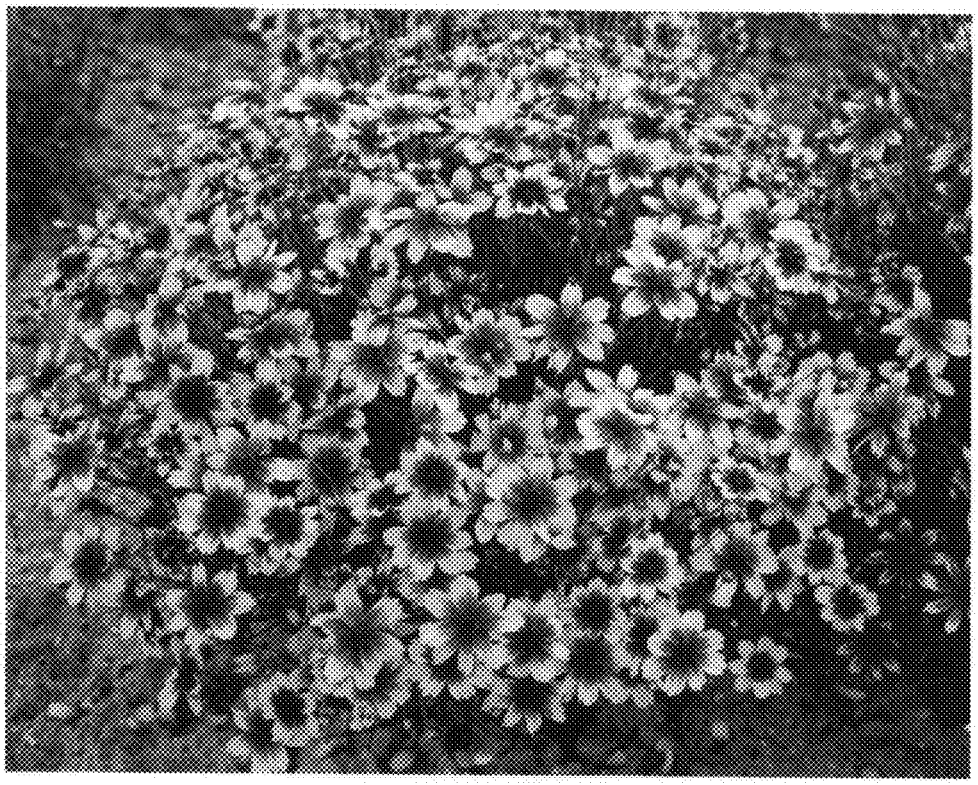

The photograph in FIG. 2 provides a top view of a plant of 'Peach Sparkle' in bloom.

Figure 3:
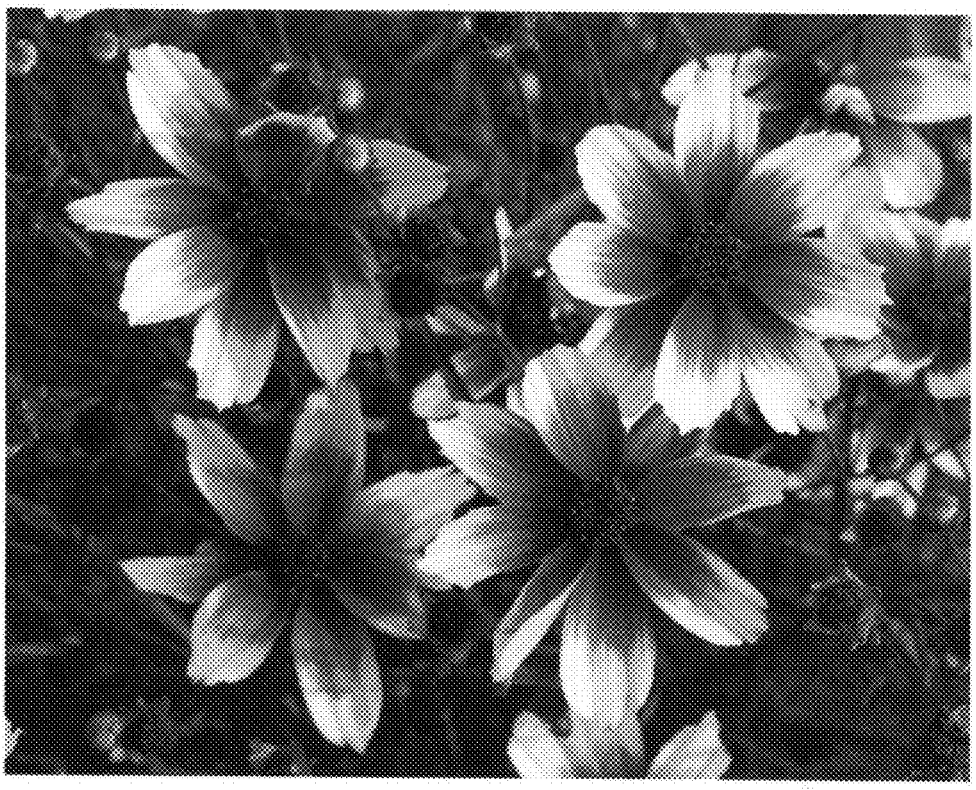

The photograph in FIG. 3 provides a close-up view of the inflorescences of 'Peach Sparkle'.

The colors in the photographs are as close as possible with the digital photography techniques available, the color values cited in the detailed botanical description accurately describe the colors of the new *Coreopsis*.

DETAILED BOTANICAL DESCRIPTION

The following is a detailed description of three month-old plants of 'Peach Sparkle' as grown outdoors in one-gallon containers from a 30-cell plug in Kensington, Conn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms from early July until frost in Connecticut.

*Plant type.*—Herbaceous perennial.

*Plant habit.*—Clump-forming, densely branched, compact.

*Height and spread.*—An average of 45 cm in height and width.

*Cold hardiness.*—At least in U.S.D.A Zone 5.

*Diseases resistance.*—Has been observed to be highly resistant to powdery mildew (*Podosphaera macularis*) and leaf spot (*Pseudomonas cichorii*).

*Root description.*—Fibrous when young, becoming fleshy with age.

*Propagation.*—Stem cuttings.

*Growth rate.*—Moderate.

Stem description:

*Shape.*—Oval.

*Stem color.*—137A.

*Stem size.*—Main and secondary stems; an average of 22 cm in length and 2 mm in width, secondary, tertiary stems; 10 cm in length and 1 mm in width.

*Stem surface.*—Glabrous.

*Stem aspect.*—Upright.

*Branching habit.*—Well-branched, an average of 1 main branch, 4 secondary branches per main stem, and 3 tertiary branches.

*Internode length.*—An average of 4 cm.

Foliage description:

*Leaf division.*—Simple.

*Leaf margins.*—Entire to trifid.

*Leaf size.*—Variable, up to 5.5 cm in length and 4 mm in width when entire and up to 5 cm in length and 2 cm in width when trifid.

*Leaf shape.*—Linear to ensiform.

*Leaf base.*—Clasping.

*Leaf apex.*—Acute.

*Leaf venation.*—Pinnate, inconspicuous, matches leaf color on upper and lower surface.

*Leaf attachment.*—Sessile.

*Leaf arrangement.*—Opposite.

*Leaf surface.*—Glabrous and dull.

*Leaf color.*—Upper surface; 137A, lower surface; 137D.

Inflorescence description:

*Inflorescence type.*—Composite with a single row of ray florets surrounding disk florets in the center, forming a radiant head, inflorescences are solitary and borne on branch terminals.

*Lastingness of inflorescence.*—8 to 10 days until senescence of ray flowers, longer in cool temperatures, bracts and disk flowers are persistent.

*Fragrance.*—None.

*Quantity of inflorescences.*—An average of 20 per main branch.

*Inflorescence size.*—An average of 8 mm in depth and up to 4.5 cm in diameter.

*Inflorescence buds.*—Average of 5 mm in depth and 4.5 mm in diameter, globose in shape, color; 144A to 144C.

*Peduncle.*—Average of 8 cm in length and 1 mm in width, 137D in color, glabrous surface.

*Sepals.*—An average of 8, 3.2 mm in length and 1.5 mm in width, color; 137D with margins 150D.

Involucral bracts:

*Bract number.*—8 total, 4 outer bracts and 4 inner bracts.

*Bract arrangement.*—Bracts are un-fused and overlapping surrounding the receptacle in a campanulate form and held close to lower surface of ray florets.

*Bract size.*—Outer and inner bracts; an average of 5 mm in length and 3 mm in width.

*Bract color.*—Inner bracts and outer bracts translucent; a blend of 9A to 9C and 144A to 144B.

*Bract texture.*—Glabrous on outer and inner surfaces of outer and inner bracts.

*Bract apex.*—Acute on outer and inner bracts.

*Bract base.*—Truncate on inner and outer bracts.

*Bract margins.*—Entire on outer and inner bracts.

*Bract shape.*—Ovate on outer and inner bracts.

Ray florets (sterile):

*Number.*—An average of 8 with 4 outer rays and 4 inner rays.

*Shape.*—Rotund to ovate.

*Size.*—An average of 2 cm in length and 1.2 cm in width.

*Apex.*—2 notched.

*Base.*—Cuneate.

*Margins.*—Entire with apex notched.

*Aspect.*—Held outward to upward.

*Texture.*—Glabrous on upper and lower surface.

*Color.*—Opening and fully open upper surface; 8A to 8C with base and thin margin 187B to 187D, opening and fully open lower surface; 9C with base 187B.

Disk flowers (perfect):

*Shape.*—Tubular, corolla is fused, flared at apex.

*Number.*—About 80.

*Size.*—About 4.5 mm in length and 0.8 mm in width.

*Color.*—En masse; 178A to 178C, corolla tube; 8B to 8D with apices 178B in color.

*Receptacle.*—About 2 mm in diameter and 1 mm in depth, 138B in color.

Reproductive organs:

*Presence.*—Disk flowers are perfect, ray flowers are sterile.

*Gynoecium.*—1 pistil, 3 mm in length, style is very fine, translucent and 8B in color, stigma is 178B in color, ovary is 1 mm in length, 1 mm in width, inferior, and 150D in color.

*Androcoecium.*—5 stamens, fused into tube surrounding style, 1 mm in length and 0.2 mm in width, about 200A to 200B in color, pollen is very low in quantity, too little to determine color.

*Fruit/seed.*—No fruit or seed development was observed.

It is claimed:

1. A new and distinct cultivar of *Coreopsis* plant named 'Peach Sparkle' as herein illustrated and described.

* * * * *